United States Patent [19]

Lee et al.

[11] Patent Number: 5,378,730

[45] Date of Patent: Jan. 3, 1995

[54] PERMEATION ENHANCER COMPRISING ETHANOL AND MONOGLYCERIDES

[75] Inventors: Eun S. Lee, Redwood City; Su Il Yum, Los Altos, both of Calif.

[73] Assignee: Alza Corporation, Palo Alto, Calif.

[21] Appl. No.: 985,530

[22] Filed: Dec. 3, 1992

Related U.S. Application Data

[63] Continuation of Ser. No. 703,000, May 20, 1991, abandoned, which is a continuation-in-part of Ser. No. 592,712, Oct. 4, 1990, abandoned, which is a continuation-in-part of Ser. No. 482,625, Feb. 21, 1990, abandoned, which is a continuation-in-part of Ser. No. 474,741, Feb. 8, 1990, abandoned, and a continuation-in-part of Ser. No. 204,808, Jun. 9, 1988, abandoned.

[51] Int. Cl.$^6$ ............... A61K 31/24; A61K 31/70; A61K 31/60; A61K 31/22

[52] U.S. Cl. .................... 514/535; 514/23; 514/159; 514/546; 514/560; 514/786

[58] Field of Search ............ 514/546, 786, 535, 560, 514/159, 23

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,031,894 | 6/1977 | Urquhart et al. | 128/268 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,460,372 | 7/1984 | Campbell et al. | 604/896 |
| 4,568,343 | 2/1986 | Leeper et al. | 604/896 |
| 4,820,720 | 4/1989 | Sanders et al. | 514/356 |
| 4,863,970 | 9/1989 | Patel et al. | 514/784 |

FOREIGN PATENT DOCUMENTS 1001949  8/1965  Germany ................ A61K 3/00

OTHER PUBLICATIONS

Idson B., "Percutaneous Absorption", Journal of Pharmaceutical Sciences, vol. 64, No. 6 (Jun. 1975), pp. 901–924.

*Primary Examiner*—Marianne M. Cintins
*Assistant Examiner*—K. Weddington
*Attorney, Agent, or Firm*—Alisa A. Harbin; Edward L. Mandell; Steven F. Stone

[57] ABSTRACT

Mixtures of ethanol and monoglyceride are disclosed for enhancing the permeation of drugs through skin or mucosa. The monoglyceride is a monoglyceride or a mixture of monoglycerides of fatty acids with a total monoesters content of at least about 90%. Water is also included in the permeation-enhancing mixture.

12 Claims, 7 Drawing Sheets

PERMEATION ENHANCER COMPRISING ETHANOL AND MONOGLYCERIDES

CROSS-REFERENCE TO RELATED APPLICATION

This application is a continuation, of application Ser. No. 07/703,000, filed May 20, 1991, now abandoned and benefit of the filing date of said earlier filed application is claimed under 35 U.S.C. §120, which is a continuation-in-part of application Ser. No. 07/592,712, filed Oct. 4, 1990, now abandoned which is a continuation-in-part of application Ser. No. 07/482,625, filed Feb. 21, 1990, now abandoned, which is a continuation-in-part of application Ser. No. 07/474,741, filed Feb. 8, 1990 now abandoned and a continuation-in-part of application Ser. No. 07/204,808, filed Jun. 9, 1988, now abandoned, the disclosures of which are incorporated herein by reference, which applications are assigned to ALZA Corporation and benefit is claimed of their filing dates.

FIELD OF THE INVENTION

This invention relates to the transdermal delivery of drugs and other biologically active agents. More particularly, this invention relates to novel methods and compositions for enhancing the percutaneous absorption of drugs when incorporated in transdermal drug delivery systems. Still more particularly, but without limitation thereto, this invention relates to the transdermal delivery of drugs utilizing a permeation-enhancing mixture of monoglycerides and ethanol, optionally in water.

BACKGROUND OF THE INVENTION

The transdermal route of parenteral delivery of drugs provides many advantages over other administrative routes, and transdermal systems for delivering a wide variety of drugs or other beneficial agents are described in U.S. Pat. Nos. 3,598,122, 3,598,123, 4,379,454, 4,286,592, 4,314,557 and 4,568,343, for example, all of which are incorporated herein by reference. In many instances, drugs which would appear to be ideal candidates for transdermal delivery are found to have such low permeability through intact skin that they cannot be delivered at therapeutically effective rates from reasonably sized systems.

In an effort to increase skin permeability, it has been proposed to pretreat the skin with various chemicals or to concurrently deliver the drug in the presence of a permeation enhancer. Various materials have been suggested for this purpose, as described in U.S. Pat. Nos. 3,472,931, 3,527,864, 3,896,238, 3,903,256, 3,952,099, 4,046,886, 4,130,643, 4,130,667, 4,299,826, 4,335,115, 4,343,798, 4,379,454, 4,405,616 and 4,746,515, all of which are incorporated herein by reference; British Pat. No. 1,001,949; and Idson, Percutaneous Absorption, J. Pharm. Sci., vol. 64, No. b6, June 1975, pp 901-924 (particularly 919-921).

To be considered useful, a permeation enhancer should have the ability to enhance the permeability of the skin for at least one and preferably a significant number of drugs. More importantly, it should be able to enhance the skin permeability such that the drug delivery rate from a reasonably sized system (preferably 5–50 cm$^2$) is at therapeutic levels. Additionally, the enhancer, when applied to the skin surface, should be non-toxic, non-irritating on prolonged exposure and under occlusion, and non-sensitizing on repeated exposure. Preferably, it should be odorless and capable of delivering drugs without producing burning or tingling sensations.

The present invention greatly increases drug permeability through the skin, and also reduces the lag time between application of the drug to the skin and attainment of the desired therapeutic effect.

While it is known in the art to combine permeation enhancers, this invention utilizes a novel combination of ethanol and a mixture of monoglycerides with a total monoesters content of at least 90%. The combined effect produces a significant and surprising improvement over use of not only either monoglyceride or ethanol alone but also over the combination of ethanol and a monoglyceride such as glycerol monooleate (GMO) of lesser purity and lower monoesters content.

SUMMARY OF THE INVENTION

It is an object of this invention to increase the permeability of body surfaces of animals and humans, particularly the skin, by the concurrent application to the body surface of a drug and of a permeation-enhancing mixture, the mixture comprising ethanol and a monoglyceride or a mixture of monoglycerides of fatty acids with a total monoesters content of at least 90%. A covehicle such as water may optionally be, and preferably is, included in the composition.

The system of the invention comprises a carrier or matrix adapted to be placed in drug- and permeation-enhancing mixture-transmitting relation to the selected skin or other body site. The carrier or matrix contains sufficient amounts of drug and the permeation-enhancing mixture to continuously coadminister to the site, over a predetermined delivery period, the drug, in a therapeutically effective amount, and the permeation-enhancing mixture, in an amount effective to enhance the permeation of the skin to the drug.

As used herein, the term "transdermal" delivery or application refers to the delivery or application of agents by passage through skin, mucosa and/or other body surfaces by topical application or by iontophoresis.

As used herein, the term "therapeutically effective" amount or rate refers to the amount or rate of drug or active agent needed to effect the desired therapeutic result.

As used herein, the terms "monoglyceride" and "monoglyceride mixture" refer to a monoglyceride or a mixture of monoglycerides of fatty acids with a total monoesters content of at least about 90%.

As used herein, the term "monoesters" refers to those monoesters having from 10 to 20 carbon atoms.

BRIEF DESCRIPTION OF THE DRAWINGS

The invention will be described in further detail with reference to the accompanying drawings wherein.

DESCRIPTION OF THE INVENTION

This invention codelivers ethanol and a monoglyceride or a mixture of monoglycerides of fatty acids with a total monoesters content of at least 90% to aid in delivery of drugs across the skin. While both ethanol and certain monoglycerides are known permeation enhancers, their combined effect according to this invention has been shown to produce dramatic increases (in the order of 10-20 times or even higher) in the permeation of drugs when compared to the use of either ethanol or a particular monoglyceride, such as glycerol monooleate or glycerol monolaurate, alone. Improved enhancement of permeation according to this invention can be obtained over a relatively wide range of ethanol/monoglyceride weight ratios. This invention contemplates ethanol/monoglyceride weight ratios in the range of from about 5/95 to about 97/3 and preferably in the range of from about 80/20 to about 40/60.

Fatty acids may be saturated or unsaturated and straight chained and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. In a preferred embodiment of this invention, the permeation enhancer is a monoglyceride or a mixture of monoglycerides of unsaturated fatty acids, and more preferably it is a monoglyceride or a mixture of monoglycerides with glycerol monooleate or glycerol monolinoleate, more preferably glycerol monooleate, predominating.

Prior to the present invention, monoglycerides have generally been available as a mixture of monoglycerides, with the mixture deriving its name from the monoglyceride present in the greatest amount. The total monoesters content has generally been relatively low. For example, prior to this invention, glycerol monooleate was commercially available as a mixture of glycerol oleates, with the monooleate being the principle component in an amount generally of about 45-60% and with the total monoesters content of the mixture being less than 60%. This mixture is indicated as "old GMO" herein. One example of a commercial prior monoglyceride is Emerest ® 2421 (Emery Division, Quantum Chemical Corp.), which is a mixture of glycerol oleates with a glycerol monooleate content of 58% and a total monoesters content of 58%. It has now been found that a mixture of monoglycerides of fatty acids with a total $C_{10-20}$ monoesters content of 90% or greater gives surprisingly improved characteristics to the compositions of the present invention. Examples of such monoglycerides are Myverol ® 18-99K (Eastman Chemical Products) which has a glycerol monooleate content of 61% and a total monoesters content of 93%, and Myverol ® 18-92K which has a glycerol monolinoleate content of 68% and a minimum total monoesters content of 90%.

Figure 12:
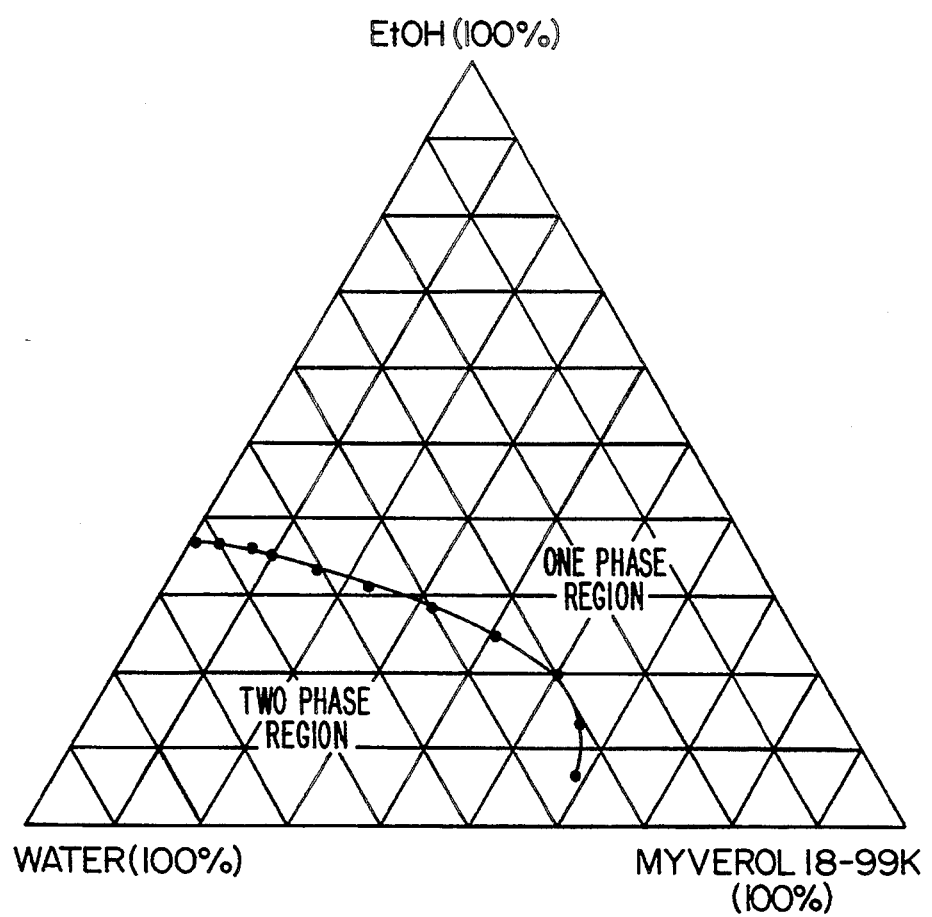
FIG. 12 is a three-component phase diagram showing the soluble and insoluble ranges for mixtures of ethanol, monoglyceride (Myverol®18-99K; 61% glycerol monooleate, total monoesters of 93%), and water at 24° C.

Surprisingly, monoglyceride (that is, a monoglyceride or a mixture of monoglycerides of fatty acids with a total $C_{10-20}$ monoesters content of about 90% or greater) and ethanol, when included in combination with water, provides a single liquid phase over a greatly increased range of ethanol/monoglyceride/water weight ratios as compared to the combination of ethanol, "old GMO" and water. It has been found that the compositions of the invention when present as a single phase give much greater enhancement of drug flux. Thus, the presence of water in the permeation-enhancing mixture of the invention has a decided beneficial effect on the enhancement of skin permeation of a drug when in combination with ethanol and monoglyceride and is not simply present as an inert, inactive component, such as a diluent. The single liquid phase will be present over a varying range of ethanol/monoglyceride/water weight ratios, depending on the total monoglycerides and monoesters content of the monoglyceride mixture. For example, Myverol 18-99K (a monoglyceride mixture encompassed by the present invention) provides a single liquid phase over a greatly increased range as compared to Emerest 2421 (an "old GMO" monoglyceride mixture not encompassed by the present invention). See, FIGS. 7 and 12, which are three-component phase diagrams for mixtures of ethanol, water and either Emerest 2421 (FIG. 7) or Myverol 18-99K (FIG. 12). Additionally, the resulting increased single-phase range makes possible a greater percentage of water in the composition, which is advantageous because it reduces irritation which may be caused by the ethanol and/or the monoglyceride. Also, the increased water content makes it easier to form a gel with the composition.

It has also now been found that there is an "optimum range" of water content in the permeation-enhancing mixture at which drug permeation is particularly enhanced. This range plays an important role in the synergistic enhancement of permeation by ethanol and a monoglyceride. Thus, while there is enhanced permeation of a drug when the water is present in amounts both below and above the optimum range, the permeation is substantially increased when the water is present in an amount that falls within this optimum range. Therefore, in a preferred embodiment of this invention, the water content in the permeation-enhancing mixture will be within this optimum range. This range will vary depending on the drug used, on the ratio of ethanol to monoglyceride in the enhancer mixture, and on the particular monoglyceride or mixture of monoglycerides chosen. Such optimum range can be determined by those skilled in the art without undue experimentation from methods known in the art or as taught herein.

The ratio, by weight, of the ethanol-and-monoglyceride mixture to water is from about 96/4 to about 20/80, preferably from about 85/15 to about 40/60.

The present invention, therefore, in one embodiment is directed to a composition of matter for application to a body surface or membrane to administer a drug by permeation through the body surface or membrane, the composition comprising, in combination:

(a) the drug to be administered, in a therapeutically effective amount; and
(b) a permeation-enhancing mixture comprising:
 (i) 3-95% by weight of a monoglyceride or a mixture of monoglycerides of fatty acids with a total $C_{10-20}$ monoesters content of at least 90%,
 (ii) 5-97% by weight of ethanol, and
 (iii) 0-60% by weight of water.

The drug may be present in the composition in an amount ranging from about 0.01 to about 50% by weight, preferably in an amount which is equivalent to the solubility or saturation of the drug in the permeation-enhancing mixture.

This invention finds particular usefulness in enhancing permeability across skin. However, it is also useful in enhancing flux across mucosa. Further, this invention is useful in delivery of both systemically and topically active drugs. According to our invention, the permeation-enhancing mixture and the drug to be delivered are placed in drug- and permeation-enhancing mixture-transmitting relationship to the appropriate body surface, preferably in a pharmaceutically acceptable carrier therefor, and maintained in place for the desired period of time. The drug and the permeation-enhancing mixture are typically dispersed within a physiologically compatible matrix or carrier as more fully described below which may be applied directly to the body as an ointment, gel, cream, suppository or sublingual or buccal tablet, for example. When the ethanol and the monoglyceride are dispersed in a liquid vehicle for topical application to the skin, greater enhancement of drug flux has been observed when the concentration of ethanol, the monoglyceride mixture and the vehicle are selected such that a single liquid phase exists for these components. When used in the form of a liquid, ointment, lotion, cream or gel applied directly to the skin, it is preferable, although not required, to occlude the site of administration to prevent evaporation of the ethanol and other volatile components such as water. Such compositions can also contain other permeation enhancers such as sucrose monococoate and salicylic acid, stabilizers, dyes, diluents, pigments, vehicles, inert fillers, excipients, gelling agents, vasoconstrictors, and other components of topical compositions as are known to the art.

In other embodiments, the drug and permeation enhancers would be administered from a transdermal delivery device as more fully described below.

In one embodiment, the device administering an excess of drug to the skin and at least one of the ethanol or monoglyceride mixture is coadministered at a controlled preferably substantially constant rate. The rate of drug administration is determined by the rate of administration of the enhancer, which enhancer rate is intentionally controlled. In this embodiment, the dosage form could comprise a body:

(a) having a basal surface
 (i) of area at least about equal to the area of skin to be treated,
 (ii) that is adapted to contact the area of skin over the time period, and
 (iii) via which the drug and enhancers are presented to
the area of skin for the absorption thereby;
(b) containing a supply of the drug that communicates with the basal surface to provide drug at the basal surface over the time period;
(c) containing supplies of monoglyceride mixture and ethanol which communicate with the basal surface so as to provide the enhancers at the basal surface over said time period; and
(d) optionally including means for maintaining the rate at which at least one of the monoglyceride mixture or ethanol is provided at the basal surface.

In one embodiment, the supply of drug is such that over a substantial portion of the time period, the amount of drug provided to the basal surface is in excess of that which the area of treated skin is able to absorb, and the rate at which one of the monoglyceride mixture or ethanol is provided is substantially constant over a substantial portion of the time period, the rate being:
(i) below the maximum rate the area of skin is able to absorb, and
(ii) sufficient with the coadministration of the other enhancer to substantially increase the permeability of the area of skin to the drug.

In a permeation-enhancing system such as that of the present invention, when one of the permeation enhancers absorbs more quickly into the skin or otherwise disperses from the dosage form more rapidly than the second permeation enhancer, it is desirable to include a means for maintaining the desired ratio of first enhancer to second enhancer in the system for the entire duration of application to the skin. This is of particular importance when maintenance of a single liquid phase is desired. Therefore, one embodiment of the invention is directed to a dosage form for transdermally administering a drug, a first enhancer and a second enhancer to the skin of a patient, the dosage form comprising:

a) a body containing a supply of drug, first enhancer and second enhancer;
b) means for maintaining the body in drug-, first enhancer-and second enhancer-transmitting relationship to the skin; and
c) means for replenishing the supply of the first enhancer to maintain a desired ratio of first enhancer to second enhancer in transmitting relationship to the skin.

The method of this invention comprises:
(a) administering a drug, in a therapeutically effective amount, to the area of skin over the time period; and
(b) coadministering a permeation-enhancing mixture according to this invention to the area of skin.

In a preferred embodiment of the permeation-enhancing mixture of the invention, the monoglyceride mixture and ethanol are combined together with water and the combination is in a single liquid phase.

As used herein, the term "substantial portion of the time period" means at least about 60% of the time period, preferably at least about 90% of the time period. Correlatively, the term "substantially constant" means a variation of less than about +20% preferably less than about ±10%, over a substantial portion of the time period.

It is believed that this invention has utility in connection with the delivery of drugs within the broad class normally delivered through body surfaces and membranes, including skin. As used herein, the expressions "drug" and "agent" are used interchangeably and are intended to have their broadest interpretation as to any therapeutically active substance which is delivered to a living organism to produce a desired, usually beneficial, effect. In general, this includes therapeutic agents in all of the major therapeutic areas, including, but not limited to, anti-infectives such as antibiotics and antiviral agents, analgesics and analgesic combinations, anorexics, antiarthritics, antiasthmatic agents, anticonvulsants, antidepressants, antidiabetic agents, antidiarrheals, antihistamines, steroidal anti-inflammatory agents, nonsteroidal anti-inflammatory agents, antimigraine preparations, antimotion sickness preparations, antinauseants, antineoplastics, antiparkinsonism drugs, antipruritics, antipsychotics, antipyretics, antispasmodics including gastrointestinal and urinary, anticholinergics, sympathomimetrics, xanthine derivatives, cardiovascular preparations including calcium channel blockers, beta-blockers, antiarrythmics, antihypertensives, diuretics, vasodilators including general, coronary, peripheral and cerebral, central nervous system stimulants, cough and cold preparations, decongestants, diagnostics, hormones such as estrogens and progestogens, hypnotics, immunosuppressives, muscle relaxants, parasympatholytics, parasympathomimetrics, psychostimulants, sedatives and tranquilizers.

We have demonstrated the utility of mixtures of ethanol and a monoglyceride or monoglyceride mixture as a permeation enhancer for several dissimilar drugs within these classes such as testosterone, hydrocortisone, tetracaine, lidocaine, ketoprofen, piroxicam, propranolol, indomethacin, naproxen, nisoldipine, nifedipine, nicardipine, nitrendipine and diclofenac. We also believe the combination to be applicable to an even larger number of drugs. Representative drugs include, by way of example and not for purposes of limitation, scopolamine, isosorbide dinitrate, nitroglycerin, estradiol, clonidine, cortisone, theophylline, phenylephrine, terbutaline, ephedrine, narcodine, quinidine, estradiol diacetate, progesterone, pilocarpine, furosemide, tetracycline, insulin, chlorpheniramine, sulfathiazides, norgestrel, morphinone, morphine, dihydrocodeine, dihydromorphine, oxycodone, hydrocodone, codeine, norcodeine, hydromorphine, normorphine, norlevorphanol, dihydrothebaine, ouabain, bromocryptine, haloperidol, guanabenz, salbutamol, oxprenolol, dibucaine, verapamil, prazosin, doxazosin, diltiazem, atenolol , nadolol pindolol , timolol, indomethacin, phenylbutazone, benzydamine, and flufenamic acid.

The effect of mixtures of monoglyceride and ethanol as a permeation enhancer for any particular drug may be determined by a worker skilled in the art from in vitro permeation measurements performed on cadaver skin or other membranes in conventional diffusional cell tests as verified by in vivo measurements of blood or urine level s, for example.

Figure 1:
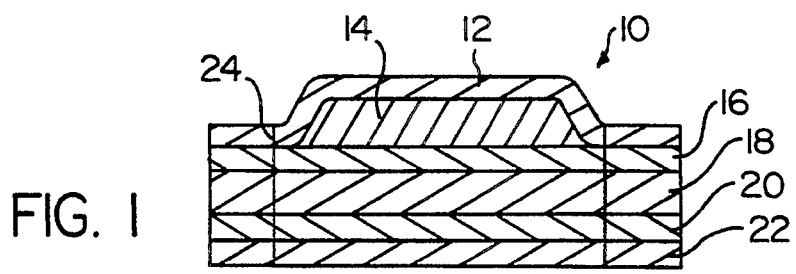
FIG. 1 is a cross-sectional view of one embodiment of the transdermal drug delivery system according to this invention, utilizing a rate-controlling membrane.

One embodiment of the invention is best understood with reference to FIG. 1, which illustrates a transdermal drug delivery device 10. Device 10 is a multilaminate system comprised of five layers: a top impermeable backing layer 12, a permeation enhancer reservoir layer 14, a permeation enhancer rate-controlling membrane 16, a drug reservoir 18, an adhesive layer 20 and a strippable release liner 22. The reservoir 14 may be comprised of a gel or polymeric matrix or other carrier having the permeation enhancer or drug to be delivered dispersed throughout.

Device 10 is held in place by means of an in-line pharmaceutically acceptable contact adhesive 20. An additional loading of the drug, monoglyceride mixture and/or ethanol may also be incorporated into the adhesive layer 20. The composition and thickness of the adhesive layer are preferably selected such that the layer does not constitute a significant permeation barrier to the drug, monoglyceride mixture or ethanol. During the time interval between the manufacture and use of the system 10, adhesive layer 20 with the other layers will equilibrate and will contain monoglyceride mixture, ethanol and drug in amounts that will depend upon the composition and thickness of layer 20 and the length of the time interval. Contact adhesive compositions that are suitable for use as layer 20 are disclosed in U.S. Pat. Nos. 3,797,494 and 4,031,894. A strippable release liner 22, adapted to be removed prior to application, would normally be included in the packaged product.

Reservoir 14 may comprise a homogeneous monoglyceride/ethanol phase, which may also contain one or more covehicles, such as water. Preferably the homogeneous phase is in the form of a gel that can contain from about 5 to about 75% by weight water. Known gelling agents such as carboxypolymethylene, ethylene maleic anhydride, hydroxyethylcellulose, polyacrylamide, ethylhydroxyethylcellulose, hydroxypropylcellulose, and poly (methylvinylether-maleic anhydride) may also be included in the reservoir formulation to make it gel. Layer 14 may also include diluents, stabilizers, vehicles, vasoconstrictors, and the like.

Alternately, reservoir 14 may comprise only one of the monoglyceride mixture or the ethanol rather than a homogeneous monoglyceride/ethanol phase and may also contain the drug and/or one or more covehicles. In this embodiment, it is preferable for reservoir 14 to contain the ethanol, because ethanol will tend to absorb more quickly into the skin than will the drug or the monoglyceride mixture and, thus, a source of additional ethanol is desirable. In this way, the ethanol depleted from the drug reservoir 18 by skin absorption will be replenished by the ethanol from layer 14, thus maintaining the ratio of ethanol/monoglyceride in the drug layer 18. Additionally, because a preferred embodiment is to a single liquid phase of ethanol/monoglyceride/water, the presence of a separate reservoir of ethanol for replenishment will result in continuation of the proper ratio to maintain the single phase. Such a drug reservoir comprising only one enhancer is not limited to the monoglyceride mixture or ethanol but is applicable to any dual enhancer system.

The rate-controlling membrane 16 may be fabricated from permeable, semipermeable or microporous materials which are known in the art to control the rate of agents out of delivery devices. Suitable materials include polyethylene, polyvinyl acetate and ethylene vinyl acetate copolymers.

The drug reservoir 18 will contain the drug with an equilibrium concentration of the permeation-enhancing mixture of this invention. The amount of drug in the reservoir will depend upon the rate at which the drug is absorbed by the skin from the system and the intended duration of therapy. The reservoir 18 may also include dyes, diluents, pigments, stabilizers, covehicles, inert fillers, excipients, gelling agents, and conventional components of pharmaceutical products or transdermal therapeutic systems as are known in the art.

Certain drugs are highly soluble in the permeation enhancers. In those cases, the permeation enhancer reservoir layer 14 would be initially saturated with drug to insure that the drug contained within matrix 18 will diffuse towards the skin rather than into the permeation enhancer reservoir. The loading of the drug which is ultimately to be delivered will usually be contained within the drug reservoir 18 in excess of saturation.

The size of the device of this invention can vary from less than 1 cm$^2$ to greater than 200 cm$^2$. A typical device, however, will have a size within the range of about 5-50 cm$^2$.

Various materials suited for the fabrication of the various layers are disclosed in the aforementioned patents. The matrix of the drug reservoir 18 may be an aqueous gel or an anhydrous matrix. Suitable anhydrous materials include, without limitation, natural and synthetic rubbers or other polymeric materials, thickened mineral oil, or petroleum jelly. A preferred embodiment according to this invention is fabricated from an ethylene/vinyl acetate (EVA) copolymer of the type described in U.S. Pat. No. 4,144,317, preferably those having a vinyl acetate content in the range of about 2 to 60 weight percent. Particularly good results have been obtained using an EVA copolymer of 9 to 40 weight percent vinyl acetate content.

Embodiments such as device 10 in which the drug and enhancer supplies are separate may be advantageous or necessary in instances where formulation or storage of the drug and enhancers in contact with each other is impractical or undesirable or where separation of the drug and enhancers facilitate selection of the rate-controlling membrane.

The initial loading of ethanol and the monoglyceride mixture in device 10 will depend upon the rates at which the enhancers are administered to the skin from the system to achieve the desired degree of drug permeability enhancement over the treatment period.

The backing member 12 serves the purpose of both preventing passage of the drug and permeation enhancers through the surface of the gel layer distant from the skin, and also of providing support for the system, where needed. The backing layer can be flexible or nonflexible and suitable materials include, without limitation, cellophane, cellulose acetate, ethyl cellulose, plasticized vinyl acetate-vinyl chloride copolymers, polyethylene terephthalate, nylon, high and low density polyethylene, polypropylene, metalized polyester films, polyvinylidene chloride, coated flexible fibrous backings such as paper and cloth, and aluminum foil. Such backings can be in the form of precast films or fabrics which are bonded to the reservoir by heat, adhesives or otherwise, or they can be coated onto the reservoir itself. The preferred embodiment utilizes a heat-sealable backing membrane, such that the device is sealed around its periphery to prevent evaporation of the ethanol. The heat seal is shown schematically in FIG. 1, by line 24.

In operation, device 10 is applied to a relatively non-hairy area of the skin that is preferably substantially free of wrinkles, creases or folds. Various locations on the torso, such as the flank or shoulder, provide suitable sites for the transdermal system. Once the device is placed on the skin, it will begin coadministering drug, ethanol and monoglyceride mixture to the wearer.

Figure 2:
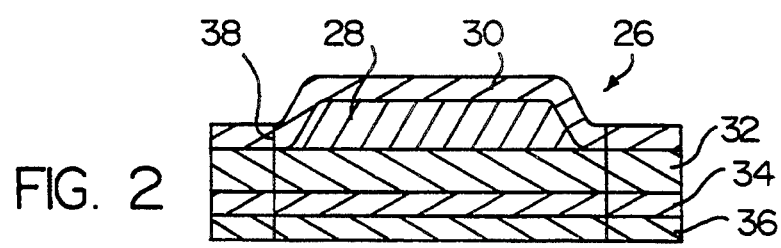
FIG. 2 is a cross-sectional view of another embodiment of the transdermal drug delivery system of this invention.

A second embodiment of the invention is shown in FIG. 2. The transdermal drug delivery device 26 comprises a permeation enhancer reservoir 28, backing member 30, drug reservoir 32, adhesive layer 34 and strippable release liner 36. In this embodiment of the invention, the rate-controlling membrane has been omitted. As with device 10, device 26 is preferably heat-sealed around its periphery, as indicated by line 38.

Figure 3:
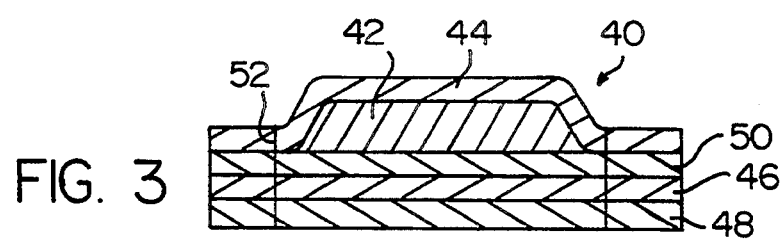
FIG. 3 is a cross-sectional view of still another embodiment of the transdermal drug delivery system according to this invention, utilizing a rate-controlling membrane.

Another embodiment of the invention is shown in FIG. 3. Device 40 incorporates the drug and the permeation enhancers into a common reservoir 42 rather than in separate reservoirs. The device has an impermeable backing 44 and a pharmaceutically acceptable in-line contact adhesive 46 which may also contain a specified amount of drug and/or permeation enhancer as a primary dose. Device 40 also has a strippable release liner 48. Device 40 is further provided with a rate-controlling membrane 50. The entire device is sealed along its periphery, as shown by line 52.

The drug will be present in the reservoir 42 either wholly in solution or in both dissolved and undissolved form dispersed uniformly through the reservoir. The initial loading of drug in layer 42 will depend on its solubility in the homogeneous phase and the intended lifetime of system 40. Layer 42 may include diluents, stabilizers, covehicles, gelling agents and the like, in addition to the drug and enhancers. This layer may also contain one or more covehicles, such as water, to alter the solubility of the drug in said phase or to provide a single liquid phase with the enhancers. Correlatively, the loading of enhancers in the reservoir will depend upon the rate at which the enhancers are administered to the skin from the system to achieve the desired degree of drug permeability enhancement over the treatment period.

Rate-controlling membrane 50 may be made of a dense or microporous polymer film that has the requisite permeability to the drug and enhancers. This membrane controls the rate at which at least one of the enhancers or the drug is administered to the skin. The respective fluxes of the drug and enhancers through layer 50 will depend upon the thickness of the layer and the permeabilities of the drug and the enhancers through the layer. Preferably, the rate-controlling membrane 50 is substantially impermeable to other components of layer 42. Examples of the types of polymer films that may be used to make layer 50 are disclosed in U.S. Pat. Nos. 3,797,494 and 4,031,894, both of which are incorporated herein by reference.

Figure 4:
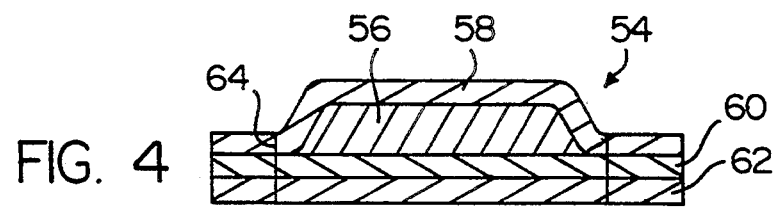
FIG. 4 is a cross-sectional view of yet another embodiment of the transdermal drug delivery system of this invention.

FIG. 4 illustrates still another embodiment of the invention, system 54, where the drug and the permeation-enhancing mixture are incorporated into a common reservoir 56. As with system 40, system 54 is comprised of an impermeable backing 58, an in-line contact adhesive 60 and a strippable release liner 62. System 54 is preferably heat-sealed around its periphery, as illustrated by line 64. In this embodiment, the rate-controlling membrane has been omitted.

Figure 5:
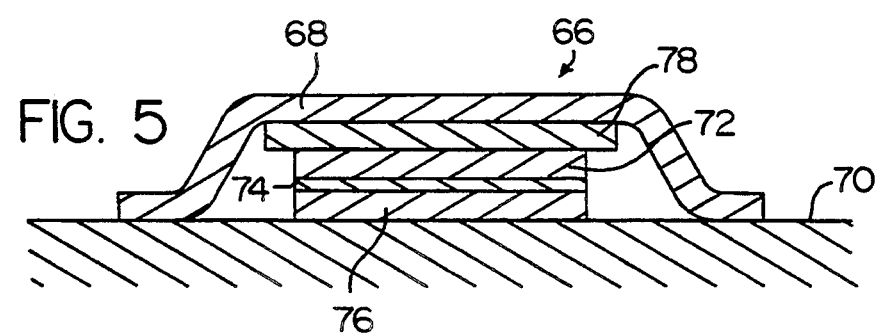
FIG. 5 is a cross-sectional view of another embodiment of the transdermal drug delivery system according to this invention, utilizing an adhesive overlay.

FIG. 5 illustrates a system 66 which provides for an adhesive overlay 68 to maintain the system on the skin 70. Means 68 for adhering the system to the skin may be fabricated together with or separately from the remaining) elements. The multilaminate system 66 is comprised of a permeation-enhancing mixture gel layer 72, a rate-controlling membrane 74 and a drug reservoir 76.

In some instances, an adhesive overlay is preferable to an in-line contact adhesive, particularly when components of the system may adversely affect the adhesive properties of an in-line adhesive. For this reason, impermeable backing layer 78 is preferably sized slightly larger than the enhancer reservoir 72 to provide a peripheral area around the reservoir 72, which would be free of any material which may seep from under the base of reservoir 72 and adversely interact with the adhesive in overlay 68. A strippable release liner would also be provided with the system 66, to be removed prior to use.

The following examples are offered to illustrate the practice of the present invention and are not intended to limit the invention in any manner.

EXAMPLE I

Several test samples were made to measure the hydrocortisone flux ($\mu g/cm^2$-hr) through human cadaver skin from donor vehicles containing an excess over saturation of hydrocortisone. The donors were water alone, ethanol alone, glycerol monooleate (GMO) mixture alone, and ethanol and GMO mixture combined, in a weight ratio of 40/60 with varying amounts of water as set forth in Table A below. The GMO mixture used was Emerest ® 2421 (from Emery Division, Quantum Chemical Corp. ) which had a GMO content of 58% and a total monoesters content of 58%.

TABLE A

| | WT % H₂O/GMO/EtOH |
|---|---|
| AA | 100/-/- |
| BB | -/-/100 |
| CC | -/100/- |
| DD | 5/57/38 |
| EE | 15/51/34 |
| FF | 20/48/32 |
| GG | 30/42/28 |

Figure 6:
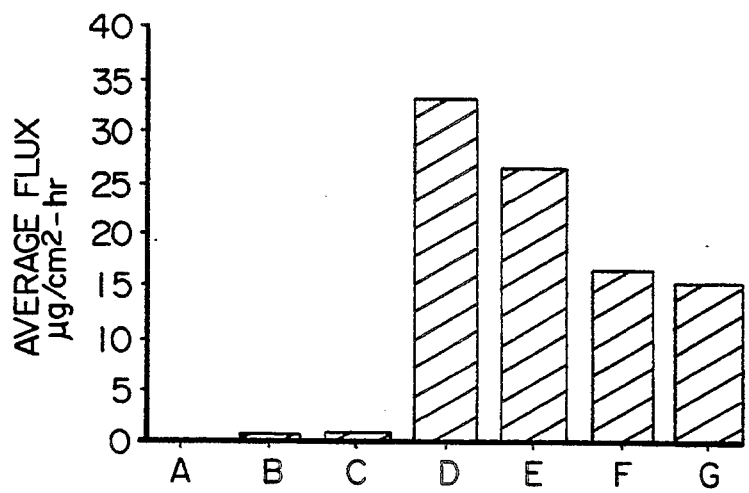
FIG. 6 is a bar chart showing transdermal flux across cadaver skin at 35° C. of hydrocortisone vs. permeation enhancer used.

Transdermal fluxes were obtained using human epidermis at 35° C. in standard diffusion cells. Samples using water, ethanol and GMO mixture separately all produced an in vitro drug flux through cadaver skin significantly less than 5 $\mu g/cm^2$-hr, whereas samples using mixtures of GMO mixture and ethanol achieved a hydrocortisone flux of more than 30 $\mu g/cm^2$-hr. The data obtained are presented graphically in FIG. 6. As can be seen, the GMO mixture/ethanol permeation enhancer produces fluxes substantially greater than those obtained from the use of GMO mixture or ethanol alone. A suitable formulation for the delivery of hydrocortisone would be comprised of about 42–76 wt % of GMO mixture and about 17–38 wt % ethanol in water containing an excess of hydrocortisone dispersed therethrough. Such formulations are capable of providing hydrocortisone fluxes within the range of 5–33 $\mu g/cm^2$-hr when applied directly to the cadaver skin.

Figure 7:
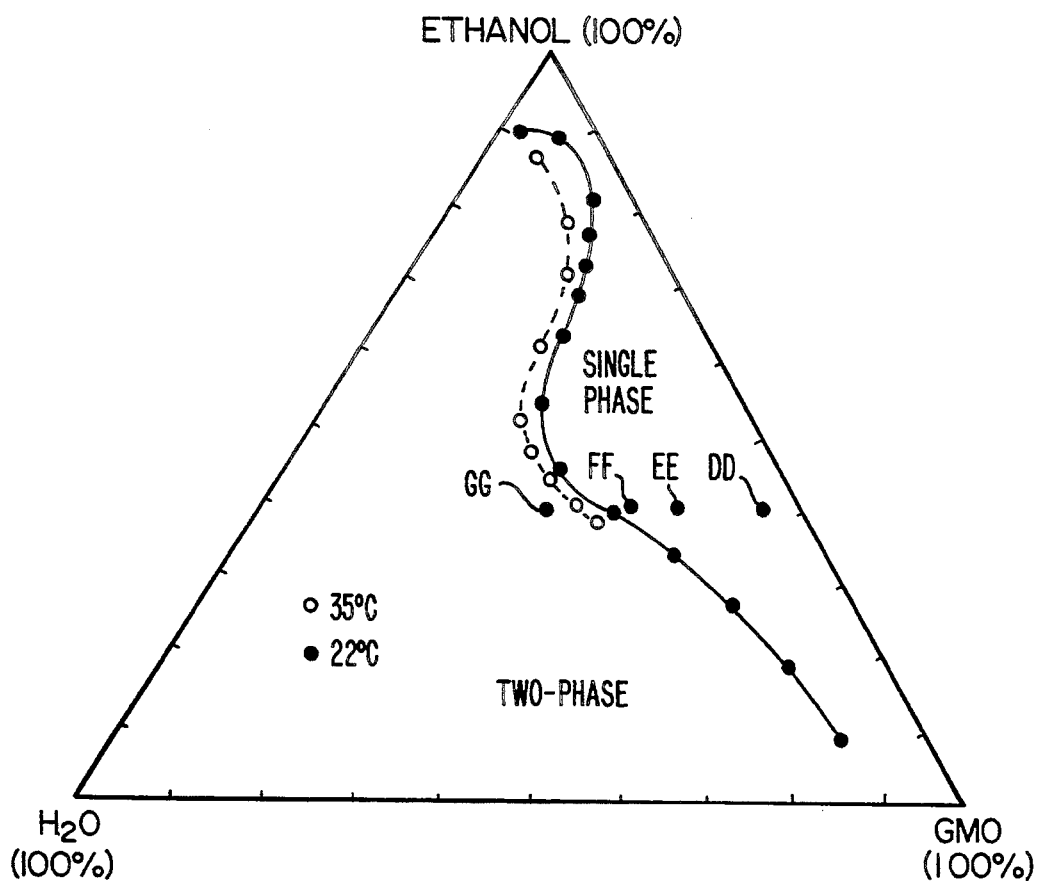
FIG. 7 is a three-component phase diagram showing the soluble and insoluble ranges for mixtures of ethanol, monoglyceride (Emerest ® 2421; 58% glycerol monooleate, total monoesters of 58%), and water at room temperature (22° C.) and at 35° C.

FIG. 7 is a phase diagram of the water/GMO mixture/ethanol system (where the GMO mixture is Emerest 2421) at room temperature (22° C.) and 35° C. on which compositions DD, EE, FF and GG have been plotted. As can be seen, compositions DD, EE and FF all fall within the portion of the diagram in which the composition exists as a single-phase solution and they all produced fluxes that were higher than that obtained from composition GG, which exists as a two-phase composition. To obtain the greatest increase in flux, the compositions can be selected such that they fall within the portion of their phase diagram in which the compositions exist as a single phase.

EXAMPLE II

A transdermal device fabricated as shown in FIG. I for the delivery of hydrocortisone would have the following composition: a Medpar ® backing layer 12; permeation enhancer reservoir 14 comprised of an ethanol gel of 98 wt % of 95% ethanol and 2 wt % of hydroxypropylcellulose; an EVA 9% VA rate-controlling membrane 16; a polymeric drug reservoir 18 comprised of 30 wt % hydrocortisone, 30 wt % monoglyceride mixture and 40 wt % EVA 40% VA; a pharmaceutically acceptable in-line contact adhesive 20; and a strippable release liner 22. During storage, all of the components will achieve a state of equilibrium so that there will be an equilibrium concentration of ethanol in the drug reservoir 18 and an equilibrium concentration of monoglyceride mixture in the permeation enhancer reservoir 14.

EXAMPLE III

Figure 8:
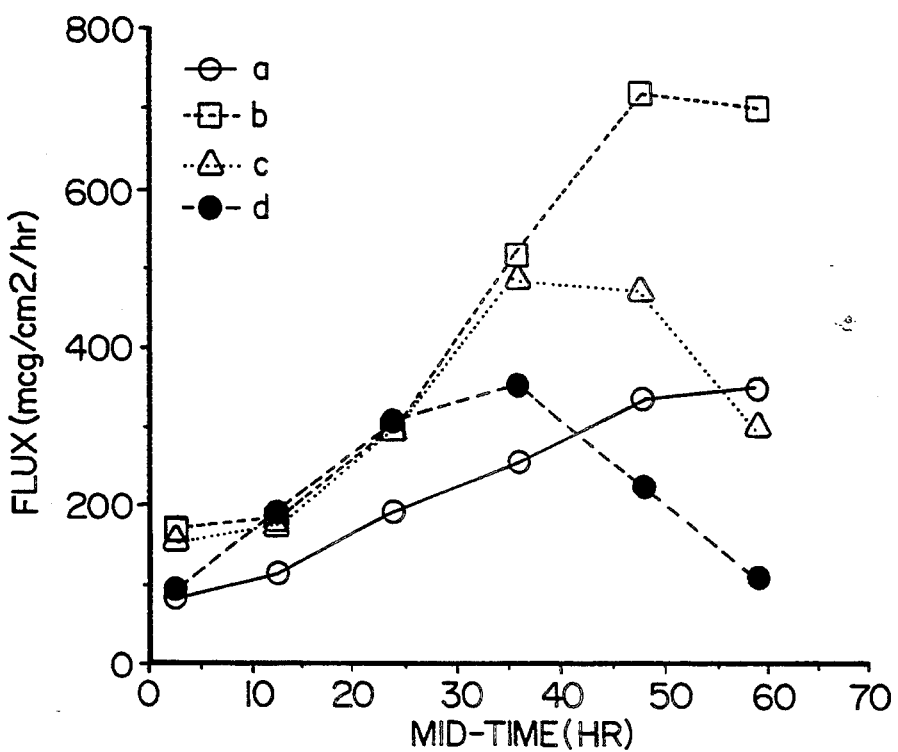
FIG. 8 is a plot showing transdermal flux across human cadaver epidermis at 35° C. of ketoprofen utilizing various permeation-enhancing mixtures of this invention.

Various ethanol/monoglyceride mixture donor compositions, in the weight ratios listed in Table B, were tested with ketoprofen to measure their effect upon the drug flux across human cadaver epidermis at 35° C. All donor compositions were saturated with the drug. Test data were obtained using a 1.13 cm² wet-wet horizontal flux cell with 0.2 ml donor solution and 20 ml receptor solutions (pH 7.4 phosphate buffer, 0.05 M), and the results are presented in FIG. 8. The monoglyceride mixture used was Myverol ® 18-99K (available from Eastman Chemical Products), which includes 61% GMO and has a total monoesters content of 93%.

TABLE B

| Donor Solution | Donor Solution Composition wt % | | |
|---|---|---|---|
| | EtOH | Monoglyceride | Water |
| a | 55.4 | 40.0 | 4.6 |
| b | 47.1 | 34.0 | 18.9 |
| c | 41.6 | 30.0 | 28.4 |
| d | 36.0 | 26.0 | 38.0 |

EXAMPLE IV

Figure 9:
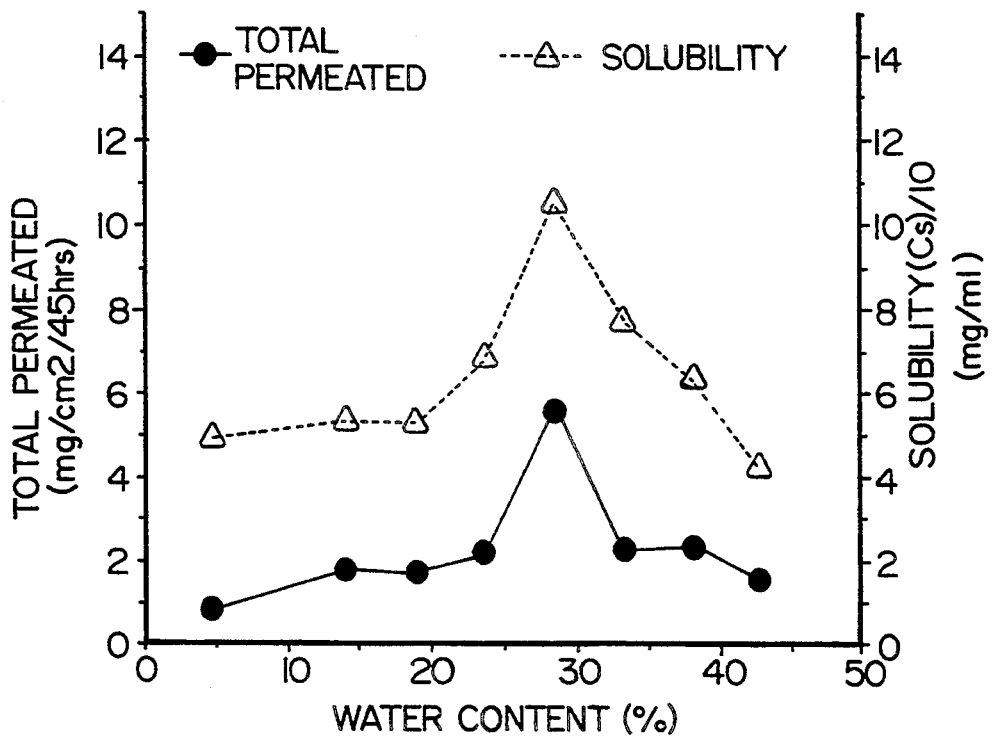
FIG. 9 is a plot showing the permeability and the solubility of piroxicam with various permeation-enhancing mixtures of this invention.

The optimum range of water in a permeation-enhancing mixture when used with the drug sodium piroxicam, where the ratio of Myverol 99K monoglyceride to ethanol is 40 to 55.4 in the mixture, was determined as follows. Various ethanol/Myverol 18-99K/water donor compositions, in the weight ratios listed in Table C, were tested with sodium piroxicam to measure their effect upon the drug flux across human cadaver epidermis at 35° C. The ratio of ethanol to monoglyceride was initially 55.4 to 40, to which varying amounts of water were added. All donor compositions were saturated with the drug. Test data were obtained using a 1.13 cm² wet-wet horizontal flux cell with 0.2 ml donor solution and 20 ml receptor solutions (pH 7.4 phosphate buffer, 0.05 M). Total drug permeated and its solubility were measured and the results are presented in FIG. 9. The results show that with sodium piroxicam and a ratio of Myverol 18-99K:ethanol of 40:55.4, the optimum range of water content in the permeation-enhancing mixture is from about 23 to about 33 wt % of water.

TABLE C

| Donor Solution | Donor Solution Composition wt % | | |
|---|---|---|---|
| | EtOH | Monoglyceride | Water |
| a | 55.4 | 40.0 | 4.6 |
| b | 49.9 | 36.0 | 14.1 |
| c | 47.1 | 34.0 | 18.9 |
| d | 44.4 | 32.0 | 23.6 |
| e | 41.6 | 30.0 | 28.4 |
| f | 38.8 | 28.0 | 33.2 |
| g | 36.0 | 26.0 | 38.0 |
| h | 33.3 | 24.0 | 42.7 |

EXAMPLE V

A transdermal device fabricated as shown in FIG. 2 for the delivery of tetracaine comprises a Medpar backing layer 30; permeation enhancer reservoir 28 comprised mainly of an ethanol gel of 98 wt % of 95% ethanol and 2 wt % of hydroxypropylcellulose; a polymeric drug reservoir 32 comprised of 30 wt % tetracaine, 30 wt % monoglyceride mixture and 40 wt % EVA 40; a pharmaceutically acceptable in-line contact adhesive 34; and a strippable release liner 36. During storage, all of the components will achieve a state of equilibrium so that there will be an equilibrium concentration of ethanol present in the drug reservoir and an equilibrium concentration of monoglyceride mixture present in the permeation enhancer reservoir 28.

EXAMPLE VI

Lidocaine is a topical anesthetic which can be used in conjunction with minor surgical procedures. When a topical ointment containing both lidocaine and prilocaine (EMLA cream, available from Astra Pharmaceutical) is applied to the skin, it has been reported that about 1–3 hours is required to achieve significant levels of local anesthesia. A vehicle composition according to this invention comprising 41.6 wt % ethanol, 30 wt % Myverol 18-99K and 28.4 wt % water was prepared, to which was added 34 wt % lidocaine base. 0.5 Gram of the mixture so formed was absorbed into a 0.75 in. diameter foam pad, applied to facial cheek skin on human volunteers and maintained in place by means of a 1,625 in. diameter adhesive overlay for either 15 minutes or 30 minutes. The sites were checked for pain by needle penetration. No pain was detected on some of the punctures and on the remaining punctures, pain was observed at a penetration of 2.5 mm, primarily at the periphery of the site. No difference between the quality of anesthesia at 15 and 30 minutes was observed.

In the same manner, the mixture was placed on forearm skin of human volunteers. The onset time of anesthesia was approximately 30 to 60 minutes, the depth of anesthesia was 1 to 2 mm, and the duration of anesthesia was at least 20 minutes.

EXAMPLE VII

The lidocaine fluxes from various permeation enhancer compositions through cadaver skin into an aqueous sink at 35° C. were compared to the flux obtained from other vehicles. The compositions identified as A, B', C and D had the following formulations, to which were added sufficient lidocaine to maintain the samples saturated with lidocaine throughout the experiment:

A. 40 wt % sucrose monococoate (SMC), 8.8 wt % ethanol, 51.2 wt % water
B'. 55.4 wt % ethanol, 40 wt % Myverol 18-99K monoglyceride mixture, 4.6 wt % water
C. 27.5 wt % Myverol 18-99K monoglyceride mixture, 38.1 wt % ethanol, 25.6 wt % water, 8.8 wt % phenethyl alcohol
D. mineral oil Combinations E through I were combinations of various of the above formulations, as follows:
E. 5.4 ml of C+2.5 ml of A
F. 40 wt % A+60 wt % B'
G. 50 wt % A+50 wt % B'
H. 60 wt % A+40 wt % B'
I. 70 wt % A+30 wt % B'

Figure 10:
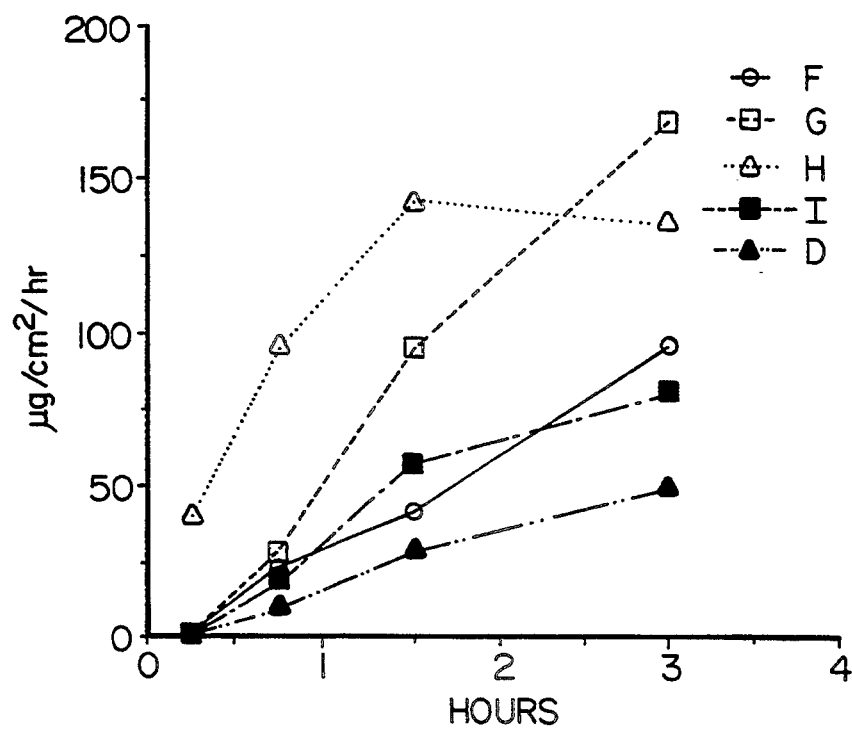
FIGS. 10 and 11 are plots showing the increased skin permeability obtained for lidocaine with certain permeation enhancers.
Figure 11:
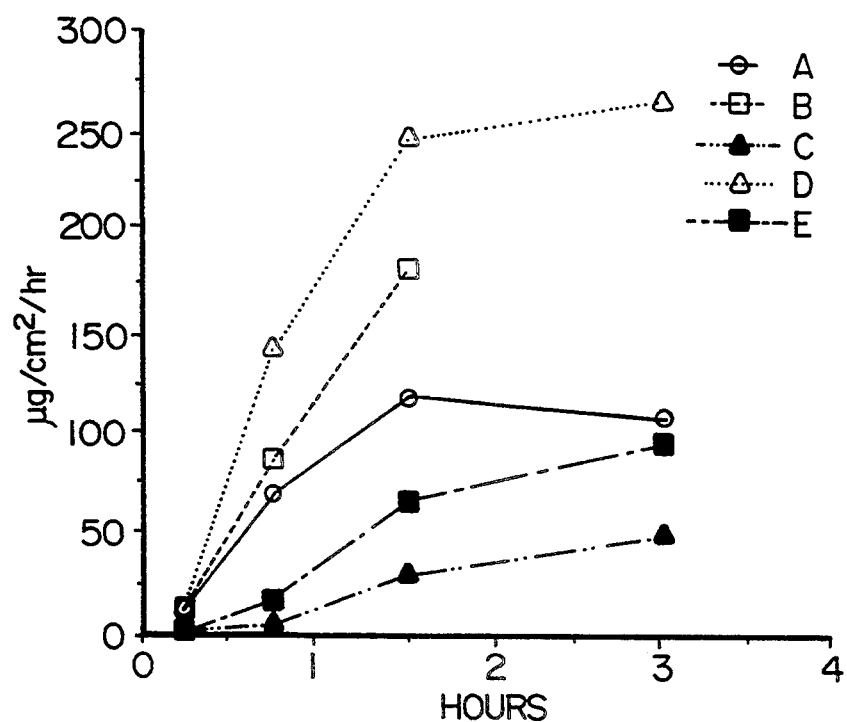

The results of one set of experiments is shown in FIGS. 10 and 11. As can be seen, the highest overall lidocaine flux was obtained from compositions C and B'. Significant improvement in permeation was also observed from various mixtures of compositions C or B'and A (which contains another known permeation enhancer, SMC). This illustrates that the use of other permeation enhancers in combination with the ethanol/monoglyceride permeation-enhancing mixture of this invention is also contemplated according to this invention.

EXAMPLE VIII

A transdermal device according to FIG. 5 for delivery of a therapeutic agent would comprise: a Medpar backing layer 44; an enhancer/drug reservoir 42 which would be comprised mainly of a single-phase solution of 95% ethanol and monoglyceride mixture in water having an excess of the drug to be delivered dispersed therethrough; an EVA 9 rate-controlling membrane 50; a pharmaceutically acceptable in-line contact adhesive 46; and a strippable release line 48.

EXAMPLE IX

A transdermal device as shown in FIG. 1 for delivery of testosterone comprises a polyester/EVA backing layer 12; a permeation enhancer reservoir 14 comprised of a mixture of 4 wt % testosterone and 96 wt % ethanol (80%); an EVA 12% VA rate-controlling membrane 16 (1.5 mil); a drug reservoir 18 comprised of 2 wt % testosterone, 18 wt % monoglyceride mixture, 40 wt % EVA 40 VA, and 40 wt % low molecular weight (35,000) polyisobutylene (LMMS); and a siliconized polyester release liner 22 (5 mil).

EXAMPLE X

A phase diagram of ethanol/Myverol 18-99K monoglyceride/water at 24° C. was determined and is shown in FIG. 12. A comparison of FIG. 12 with FIG. 7 shows that use of a monoglyceride mixture with a total monoesters content of 93% provides a single liquid phase over a greatly increased range of ethanol/monoglyceride/water weight ratios than is provided when a monoglyceride mixture with a total monoesters content of 58% is used.

EXAMPLE XI

Formulations comprising 41.25 wt % ethanol, 27.5 wt % monoglyceride, 22.5 wt % water and 8.75 wt % phenethyl alcohol were prepared using either Emerest 2421 as the monoglyceride (Formulation I) or Myverol 18-99K as the monoglyceride (Formulation II). These were then tested as donor compositions with lidocaine to compare their effect upon the drug flux across human cadaver epidermis at 35° C. in standard diffusion cells. Mineral oil (Formulation III) was included as a control. The data obtained are presented in FIG. 13.

Figure 13:
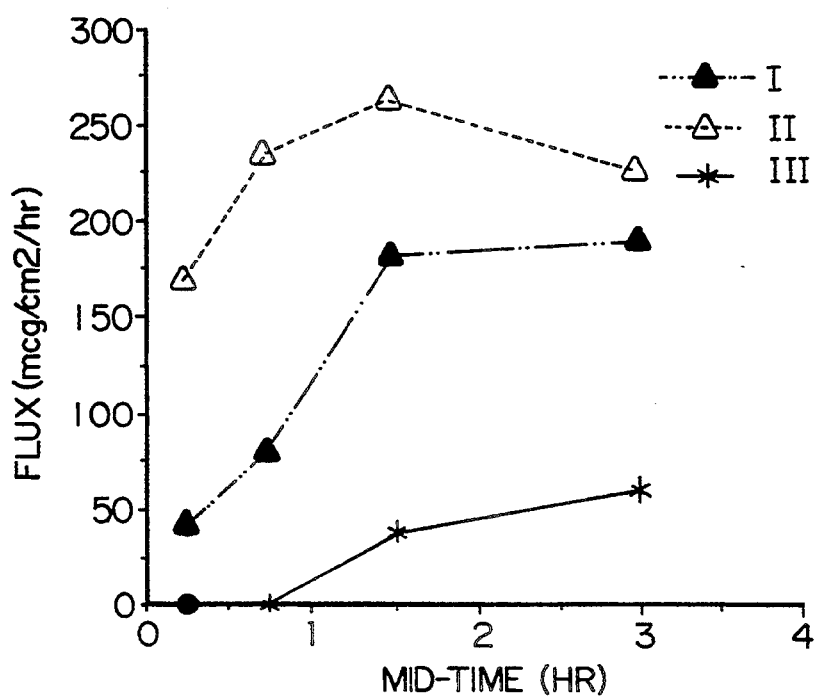
FIG. 13 is a plot showing increased skin permeability of lidocaine obtained with one embodiment of this invention.

As can be seen from FIG. 13, use of a glycerol monooleate monoglyceride mixture with a total monoesters content of at least 90% according to the present invention produces fluxes substantially greater than those of a previously used glycerol monooleate monoglyceride mixture ("old GMO") with a total monoesters content of 58%.

EXAMPLE XII

The effect of a single phase permeation-enhancing mixture as opposed to a two phase permeation-enhancing mixture on the permeation of propranolol through human cadaver epidermis was tested as follows.

Figure 14A:
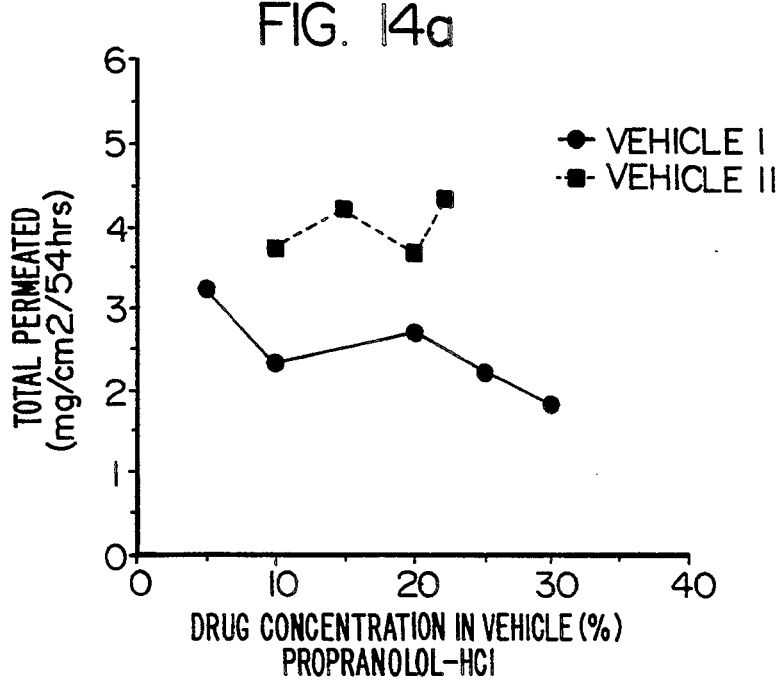
FIGS. 14a and 14b are plots showing the increased skin permeability obtained for propranolol-HCl (FIG. 14a) and propranolol base (FIG. 14b) from a single-phase enhancer mixture as compared with a two-phase enhancer mixture.
Figure 14B:
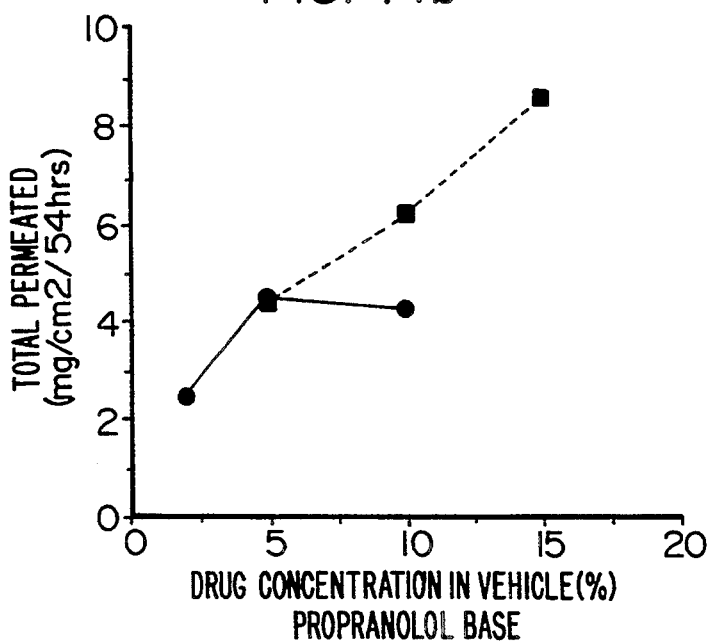

Following procedures above, different concentrations of propranolol base or propranolol-HCl were added to permeation-enhancing vehicle I or II (formulations given in Table D below, amounts in wt %), and the in vitro permeation of the drug through human cadaver epidermis was measured over 54 hours at 35° C. The results are presented in FIGS. 14a (propranolol-HCl) and 14b (propranolol base) and show that there is increased permeation of both forms of the drug with vehicle II, which was the single phase composition, over that with vehicle I, the dual phase composition.

TABLE D

|  | Vehicle I | Vehicle II |
|---|---|---|
| Ethanol | 49.0 | 41.6 |
| Emerest 2421 | 6.0 | 30.0 |
| Water | 45.0 | 28.4 |

EXAMPLE XIII

The optimum of water range in a permeation-enhancing mixture when used with the drug ketoprofen, where the ratio of Myverol 18-99K monoglyceride to ethanol is 40 to 55.4 in the mixture, was determined as follows.

Figure 15:
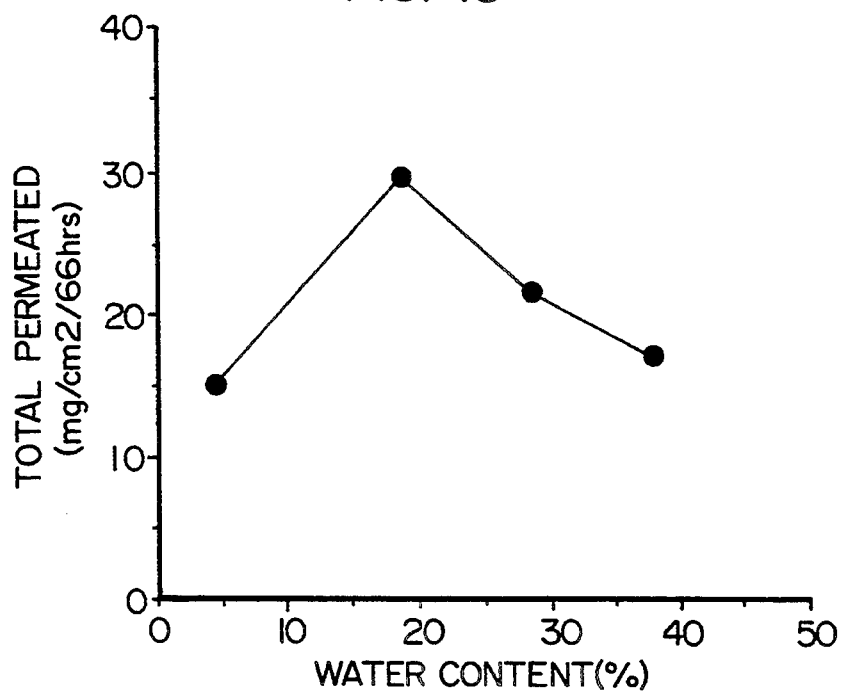
FIG. 15 is a plot showing the permeability of ketoprofen with various permeation-enhancing mixtures of this invention.

Various ethanol/Myverol 18-99K/water donor compositions were tested with ketoprofen to measure their effect upon the drug flux across human cadaver epidermis at 35° C. The ratio of ethanol to monoglyceride was initially 55.4 to 40, to which varying amounts of water were added. All donor compositions were saturated with the drug. Test data were obtained following the procedures of Example IV. Total drug permeated was measured and the results are presented in FIG. 15. The results show that with ketoprofen and a ratio of Myverol 18-99K:ethanol of 40:55.4, the optimum range of water content in the permeation-enhancing mixture is from about 10 to about 28 wt % of water.

EXAMPLE XIV

The transdermal permeation through human cadaver epidermis of two vehicle compositions of the present invention containing ketoprofen was determined and was compared to a prior art ketoprofen-containing topical ointment, Profenid ® gel (2.5% ketoprofen; Specia Rhone Poulenc).

Two vehicles according to the invention of significantly different compositions but containing the same ingredients were prepared. Vehicle composition #1 comprised 12.4 wt % ethanol, 62.3 wt % Myverol 18-99K and 25.3 wt % water; vehicle composition #2 comprised 41.6 wt % ethanol. 30.0 wt % Myverol 18-99K and 28.4 wt % water. Two wt % of hydroxypropyl cellulose was added to each vehicle as a gelling agent, after which 2.5 wt % of ketoprofen was added to each of the vehicles. Following procedures as earlier described, the two vehicles and Profenid were tested for drug permeation rate through human cadaver skin by using standard two-compartment horizontal permeation cells, at 35° C. In one test, the drug donors were occluded and in the other, they were open to the environment. The donor weight was 0.17 g/1.13 cm² of skin area. The total ketoprofen which permeated through 1.0 cm² of epidermis into a 7.4 pH phosphate receptor solution as determined over 50 hours and is presented in Table E below. The data show the superior permeation characteristics of the compositions of the present invention under both test conditions as compared to Profenid.

TABLE E

| Composition | Total Permeated (mg/cm²/50 hr) | |
|---|---|---|
|  | Non-Occluded | Occluded |
| Vehicle #1 | 1.05 | 1.4 |
| Vehicle #2 | 1.2 | 1.5 |
| Profenid | 0.6 | 0.45 |

EXAMPLE XV

The transdermal permeation through human cadaver epidermis of a vehicle composition of the present invention containing piroxicam was determined and was compared to a prior art piroxicam-containing topical ointment, Feldene ® gel (0.5% piroxicam; Pfizer).

The vehicle composition of the invention was comprised of 41.6 wt % ethanol, 30.0 wt % Myverol 18-99K and 28.4 wt % water. Piroxicam (0.52 wt % sodium piroxicam in the non-occluded system, and 0.50 wt % piroxicam in the occluded system) and 1.0 wt % of hydroxypropylcellulose (as a gelling agent) were added to the vehicle. Following procedures as described in Example XIV, the in vitro permeation of piroxicam through cadaver skin from the vehicle and from Feldene, at 35° C., were determined. The donor volume was 0.1 ml/1.13 cm² of skin area. The total piroxicam which permeated per 1.0 cm² of epidermis into an aqueous receptor solution was determined over 48 hours and is presented in Table F below. The data show the superior permeation characteristics of the composition of the present invention under both test conditions as compared to Feldene.

TABLE F

| Composition | Total Permeated (mg/cm²/48 hr) | |
|---|---|---|
|  | Non-Occluded | Occluded |
| Vehicle | 1.95 | 2.1 |
| Feldene | 0.75 | 1.6 |

EXAMPLE XVI

The drug absorption through human skin in vivo of sodium piroxicam in a gel composition containing the permeation-enhancing mixture of the present invention was determined and compared with a control (sodium piroxicam in a gel composition without the permeation-enhancing mixture).

The vehicle composition according to this invention comprised 41.6 wt % ethanol, 30.0 wt % Myverol 18-99K and 28.4 wt % water. 5.0 Weight percent sodium piroxicam and 1.5 wt % hydroxypropylcellulose (gelling agent) were then added to the vehicle (Formulation #1). The non-invention control formulation (Formulation #2) comprised 5.0 wt % sodium piroxicam and 2.0 wt % hydroxyethylcellulose (gelling agent) in 93.0 wt % water.

Approximately 0.3 to 0.4 grams of each formulation was applied to human subjects using occlusive cups over 2.5 cm² of skin area, side by side on the forearms, for 4 to 6 hours. The residual drug contents, both in the cups and on the application sites, were measured to determine the amount of drug delivered. As the results presented in Table G below show, the current invention (Formulation #1) is superior to the control in in vivo flux of the drug.

TABLE G

| Subject | Total Drug Applied (mg) | | Appln. Time (hr) | Amount Delivered (mg) | |
|---|---|---|---|---|---|
| | #1 | #2 | | #1 | #2 |
| A | 14.00 | 16.33 | 6 | 2.99 | 0.24 |
| B | 19.19 | 17.72 | 6 | 1.77 | 0.42 |
| C | 19.37 | 19.09 | 4.2 | 1.81 | 0.20 |
| Mean | 17.52 | 17.71 | 5.4 | 2.19 | 0.29 |

EXAMPLE XVII

The transdermal permeation through human cadaver epidermis of four vehicle compositions of the present invention containing diclofenac was determined and was compared to a prior art diclofenac-containing topical gel, Voltarene® Emulgel® (1.16% diclofenac diethylammonium salt; Ciba-Geigy). The 1.16% ammonium salt was equivalent to 1.0% doclofenac sodium salt or 0.93% diclofenac acid. Four vehicles according to the invention were prepared. Hydroxypropylcellulose (HPC) was added to the vehicles of formulations A, C and D; the gelling agent was not necessary in vehicle B as it was already in a gel-like form. Then, the diclofenac compound was added to each of vehicles A, B, C and D. The composition of the resulting formulations are presented in Table H below (all amounts are in weight percent).

TABLE H

| Formulation | Drug | Myverol 18-99 K | Myverol 18-92 K | EtOH, 95 vol % | Water | HPC |
|---|---|---|---|---|---|---|
| A | 1.16* | 29.06 | — | 43.58 | 24.20 | 2.0 |
| B | 1.16* | 61.24 | — | 13.86 | 23.73 | — |
| C | 1.16* | — | 29.04 | 43.59 | 24.21 | 2.0 |
| D | 0.93+ | 29.12 | — | 43.68 | 24.27 | 2.0 |
| E | 1.16* | VOLTARENE EMULGEL | | | | |

*diclofenac as the diethylammonium salt
+diclofenac as diclofenac acid

Following procedures as earlier described herein, the four compositions and Voltarene Emulgel were tested for in vitro drug permeation through human cadaver skin, at 35° C. In one test, the donor loading was 10 mg/1.13 cm2 and in a second test, the donor loading was 50 mg/1.13 cm² of skin area. All applications were non-occluded. The total diclofenac which permeated through 1.0 cm² of epidermis into a receptor solution was determined over 48 hours and is presented in Table I below. The data show the superior permeation characteristics of compositions A, C and D as compared to Voltarene Emulgel.

TABLE I

| Compositon | Total Permeated (mg/cm²/48 hr) | |
|---|---|---|
| | 10 mg/1.13 cm² | 50 mg/1.13 cm² |
| A | 0.20 | 0.83 |
| B | 0.10 | 0.42 |
| C | 0.20 | 0.65 |
| D | 0.40 | 1.17 |
| Voltarene Emulgel | 0.16 | 0.43 |

EXAMPLE XVIII

The transdermal permeation through human cadaver epidermis of four vehicle compositions of the present invention containing hydrocortisone was determined and was compared to a prior art hydrocortisone-containing topical gel, Dermolate® (0.5% hydrocortisone; Schering Corporation).

Four vehicles according to the invention were prepared. Hydroxypropylcellulose (HPC) was added to the vehicles of formulations A and C; the gelling agent was not necessary in vehicles B and D as they were already in a gel-like form. Then, the hydrocortisone compound was added to each of vehicles A, B, C and D. The compositions of the resulting formulations are presented in Table J below (all amounts are in weight percent).

TABLE J

| Formulation | Drug | Myverol 18-99 K | Myverol 18-92 K | EtOH, 95 vol % | Water | HPC |
|---|---|---|---|---|---|---|
| A | 0.51 | 29.24 | — | 43.86 | 24.37 | 2.02 |
| B | 0.50 | 61.99 | — | 13.33 | 24.18 | — |
| C | 0.50 | — | 29.20 | 43.88 | 24.42 | 2.00 |
| D | 0.50 | — | 61.44 | 13.89 | 23.97 | — |
| E | DERMOLATE | | | | | |

Following procedures as earlier described herein, the four compositions and Dermolate were tested for in vitro drug permeation through human cadaver skin. at 35° C. In one test, the donor loading was 10 mg/1.13 cm² and in a second test, the donor loading was 50 mg/1.13 cm² of skin area. All applications were non-occluded. The total hydrocortisone which permeated through 1.0 cm² of epidermis into a receptor solution was determined over 48 hours and is presented in Table L below. The data show the superior permeation characteristics of compositions A, C and D and, to a lesser extent B, as compared to Dermolate.

TABLE L

| Composition | Total Permeated (mg/cm²/48 hr) | |
|---|---|---|
| | 10 mg/1.13 cm² | 50 mg/1.13 cm² |
| A | 0.19 | 0.26 |
| B | 0.03 | 0.07 |
| C | 0.13 | 0.16 |
| D | 0.21 | 0.42 |
| Dermolate | 0.005 | 0.02 |

This invention has been described in detail with particular reference to certain preferred embodiments thereof, but it will be understood that variations and modifications can be effected within the spirit and scope of the invention.

What is claimed is:

1. A composition for application to a body surface or membrane to administer lidocaine by permeation through the body surface or membrane, the composition comprising, in combination:

(a) a therapeutically effective amount of lidocaine; and
(b) a permeation-enhancing mixture comprising:
  (i) from about 20% to about 80% by weight of a monoglyceride or a mixture of monoglycerides of fatty acids with a total $C_{10-20}$ monoesters content of at least 90%,
  (ii) from about 15% to about 75% by weight of ethanol, and
  (iii) 1–60% by weight of water.

2. A composition according to claim 1 wherein the fatty acids are unsaturated fatty acids.

3. A composition according to claim 1 wherein the permeation-enhancing mixture is in a single liquid phase.

4. A composition according to claim 2 wherein the permeation-enhancing mixture is in a single liquid phase.

5. A composition according to claim 1 wherein the permeation-enhancing mixture further comprises a material selected from the group consisting of sucrose monococoate and salicylic acid.

6. A composition for application to a body surface or membrane to administer lidocaine by permeation through the body surface or membrane, the composition comprising, in combination:
(a) a therapeutically effective amount of lidocaine; and
(b) a permeation-enhancing mixture comprising:
  (i) from about 20% to about 80% by weight of a monoglyceride or a mixture of monoglycerides of fatty acids with a total $C_{10-20}$ monoesters content of at least 90%,
  (ii) from about 15% to about 75% by weight of ethanol, and
  (iii) 1–60% by weight of water;
wherein the permeation-enhancing mixture is in a single liquid phase.

7. A composition according to claim 6 wherein the fatty acids are unsaturated fatty acids.

8. A method for administering lidocaine and a permeation-enhancing mixture to a predetermined area of skin of a patient for a predetermined time period, the permeation-enhancing mixture being comprised of 20–80 wt % of a monoglyceride or a mixture of monoglycerides of fatty acids with a total $C_{10-20}$ monoesters content of at least 90%, 15–75 wt % of ethanol and 1–60 wt % of water, the method comprising:
  a) administering lidocaine, in a therapeutically effective amount, to the area continuously over the time period; and
  b) simultaneously administering the permeation-enhancing mixture to the area of the skin at rates which are sufficient to substantially increase the permeability of the area of the skin to lidocaine.

9. A method according to claim 8 wherein lidocaine is administered at a rate in excess of that which the area of skin is able to absorb in the absence of the ethanol and the monoglyceride or mixture of monoglycerides.

10. A method according to claim 8 wherein the fatty acids are unsaturated fatty acids.

11. A method according to claim 8 wherein the permeation-enhancing mixture is in a single liquid phase.

12. A method according to claim 10 wherein the permeation-enhancing mixture is in a single liquid phase.

* * * * *